United States Patent
Guiney et al.

(10) Patent No.: US 9,984,204 B2
(45) Date of Patent: May 29, 2018

(54) MONITOR/DEFIBRILLATOR WITH BARCODE READER OR OPTICAL CHARACTER READER

(71) Applicant: KONINKLIJKE PHILIPS N.V., Eindhoven (NL)

(72) Inventors: Patrick Guiney, Concord, MA (US); William Douglas Grube, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 14/776,786

(22) PCT Filed: Mar. 12, 2014

(86) PCT No.: PCT/IB2014/059650
§ 371 (c)(1),
(2) Date: Sep. 15, 2015

(87) PCT Pub. No.: WO2014/141081
PCT Pub. Date: Sep. 18, 2014

(65) Prior Publication Data
US 2016/0034644 A1    Feb. 4, 2016

Related U.S. Application Data

(60) Provisional application No. 61/790,658, filed on Mar. 15, 2013.

(51) Int. Cl.
G06F 19/00    (2018.01)
A61N 1/39    (2006.01)

(52) U.S. Cl.
CPC ......... *G06F 19/322* (2013.01); *A61N 1/3925* (2013.01); *G16H 10/60* (2018.01); *G16H 40/63* (2018.01); *G16H 10/65* (2018.01)

(58) Field of Classification Search
CPC .............. A61N 1/36125; A61N 1/3625; A61N 1/37211; A61N 1/3993; G06F 19/30;
(Continued)

(56) References Cited

U.S. PATENT DOCUMENTS

| 6,889,903 B1 | 5/2005 | Koenck |
| 2003/0109904 A1* | 6/2003 | Silver ................ A61N 1/37211 607/59 |

(Continued)

FOREIGN PATENT DOCUMENTS

| EP | 0653723 A2 | 5/1995 |
| JP | 2008526342 A | 7/2008 |

(Continued)

*Primary Examiner* — Allen Porter, Jr.

(57) ABSTRACT

A monitor/defibrillator (100) is described having an optical image sensor (114) such as a barcode reader or an optical character reader for accurate and timely entry of information during a medical treatment event. The barcode reader or optical character reader enables a one-step capture of patient identifying information, administered therapeutic substances, equipment and other event information. The information is decoded by the monitor/defibrillator and entered into system memory for later use.

6 Claims, 7 Drawing Sheets

(58) Field of Classification Search
CPC ...... G06F 19/32; G06F 19/321; G06F 19/322; G06F 19/34; G06F 19/3406
See application file for complete search history.

(56) References Cited

U.S. PATENT DOCUMENTS

| | | | |
|---|---|---|---|
| 2003/0195567 A1* | 10/2003 | Jayne | A61N 1/39 607/5 |
| 2004/0015191 A1 | 1/2004 | Kavounas et al. | |
| 2004/0133242 A1* | 7/2004 | Chapman | A61B 5/0002 607/5 |
| 2005/0065557 A1 | 3/2005 | Powers et al. | |
| 2006/0092029 A1* | 5/2006 | Browne | A61N 1/3925 340/573.1 |
| 2008/0183229 A1* | 7/2008 | Neumiller | A61N 1/39 607/5 |
| 2011/0057037 A1 | 3/2011 | Frysz et al. | |
| 2012/0191476 A1 | 7/2012 | Reid et al. | |
| 2012/0197324 A1 | 8/2012 | Nova | |
| 2015/0213212 A1 | 7/2015 | Grimley et al. | |
| 2015/0227694 A1* | 8/2015 | Grimley | G06F 19/3406 705/3 |

FOREIGN PATENT DOCUMENTS

| | | |
|---|---|---|
| KR | 2012109181 A | 10/2012 |
| NO | 2006072869 A1 | 7/2006 |

* cited by examiner

MONITOR/DEFIBRILLATOR WITH BARCODE READER OR OPTICAL CHARACTER READER

The invention relates generally to an apparatus and method for capturing information related to a medical treatment event, and for reviewing the information after the event.

Emergency medical procedures have been studied by the medical establishment for many years. It is commonly understood that patient outcomes can be improved by modifying procedures, by eliminating harmful or unnecessary steps, or by training personnel who are not performing the procedures correctly. A typical study involves the assignment of an observer who records the time and manner of the actions taken under the medical event. In some cases, equipment which is used in the event automatically generates time-ordered logs of data as well.

In a sudden cardiac arrest medical emergency, for example, the patient is stricken with a life threatening interruption to the normal heart rhythm, typically in the form of VF or VT that is not accompanied by spontaneous circulation (i.e., shockable VT). If normal rhythm is not restored within a time frame commonly understood to be approximately 8 to 10 minutes, the patient will die. Conversely, the quicker that circulation can be restored (via CPR and defibrillation) after the onset of VF, the better the chances that the patient 14 will survive the event. It is thus a matter of great interest to the administrators who oversee the medical response organization that the rescuers perform the resuscitation quickly and effectively.

Most EMS or hospital organizations prepare incident reports of medical treatment events in order to conduct post-event reviews. Incident reports are typically constructed from manual reports filled out by on-scene observers. The reports are sometimes augmented by data automatically collected by medical devices used at the scene. The data automatically provided by a defibrillator, for example, typically includes an ECG strip, a sensed time of defibrillator activation, the initiation of CPR, delivery of defibrillation shocks, and so on. In addition, an audio record ("voice strip") that documents the verbal remarks of the first responders is often recorded by the defibrillator.

Automatically generated data, however, cannot capture all of the important information about the progress and effectiveness of the rescue. Hence there is a need for the manual report that is generated by an on-scene observer. The manual report may document information such as the names of the rescue team, the equipment used, the observed quality of CPR compressions and ventilations, drugs administered, patient responsiveness to rescue efforts, and the times of each of these events. This data must be collected and manually merged with the automatically generated data in order to provide an accurate measure of the event. All of this event data which is generated by the various sources is ideally merged together to form the incident report at a centralized computer using software such as the Event Review software, as manufactured by Koninklijke Philips, N.V., in Andover Mass.

The collection of event data during cardiac emergencies comes with a cost, however. Monitor/Defibrillators do not currently come with barcode readers or optical character readers. The traditional practice for paramedics is to treat critically ill patients, transport them to a care facility and then afterwards take time to document the patient care record. During urgent care events, paramedics do not have time to manually enter or accurately record all the information mandated by government regulations, insurance carriers and agency policies. Paramedics may scribble notes on their latex gloves or scraps of paper as a memory aid for documenting the patient care record after transport. In many cases, paramedics must rely on their own memory of chaotic events for details such as identifying a drug administered to a patient at a specific time. In recent years, healthcare reform has prompted a greater need for fidelity of information. Accurate patient care records are a prerequisite for quality assurance/quality improvement efforts, billing and the litigation that results from some patient care events.

Some solutions to the problem of accurately documenting a medical treatment have been offered. A back-of-the-ambulance data collection device is described in U.S. Patent Publication No. 2012/191476 entitled "Systems and Methods for Collection, Organization, and Display of EMS Information", in which a standard bar code reader may be used to obtain event data. Co-assigned U.S. patent application Ser. No. 14/419,408 entitled "Method and Apparatus for the Real Time Annotation of a Medical Treatment Event" describes a software application for a hand-held computing device which may capture barcode information as well as video records of a rescue. Each of these inventions, however, requires the provider to carry equipment additional to the defibrillator monitor to the scene of the rescue. The attendant workings of the additional devices tend to distract from the rescue activities.

What is needed therefore to address each of these deficiencies in the prior art is a device and method which offers a simplified data entry interface for recording important information during a medical treatment event, especially a cardiac-related event which requires the use of a portable monitor defibrillator. The interface should be capable of quickly capturing important data related to the rescue, such as the administration of drugs, identification of equipment and expiration dates, and patient data. Such a device would be particularly useful in the documentation of cardiac-related treatments.

A monitor/defibrillator having an integrated barcode or optical character reading ability overcomes the above-described problems. For example, the effort required to record identifying information into a patient record file on a prior art monitor defibrillator can require over 50 discrete actions in order to sequentially select the correct sequence of letters from a pull-down menus. In contrast, a barcode reader (BCR) or optical character reader (OCR) can acquire and decode identifying information in less than one second and in a single step. As a result, paramedics would require less time to document patient care records after transport, and utilize that time in other more efficient ways.

Also, the inaccurate recording of time associated with marked events is avoided by use of the invention. The time recorded for important patient events (e.g. drugs administered) is often inaccurately reconstructed based on the paramedic's recall of the event or through a verbal miscommunication to a recording dispatcher via radio. A monitor defibrillator with a BCR or OCR to mark events (e.g. paramedic scans barcode of administered drug vial) can automatically save and associate a time stamp from the monitor defibrillator internal clock reference with each event in the patient record file.

Also, many existing BCR formats include error correction that prevents common mistakes resulting from verbal miscommunication. For example, paramedics will have difficulty obtaining basic information (e.g. date of birth) from unresponsive patients or family members that speak a different language. A monitor/defibrillator with a BCR solves this problem by enabling the capture of basic information via a scan of an patient identification document, such as a driver's license, insurance card, etc. The device can also be enabled to immediately confirm accurate data entry.

EMS personnel often must correctly deploy consumable materials when treating patients in critical care events. Potential problems include applying incorrect type defibrillating pads to patients (e.g. pediatric vs. adult), using pads that are beyond the expiration date, administering drugs that are beyond their expiration date or using incorrect drugs altogether. A monitor/defibrillator with a barcode or optical character reader would allow a paramedic quickly capture the identifying information, e.g. lot number, material type, expiration date, etc, on consumable materials to confirm their correct application.

In accordance with the principles of the present invention, a monitor/defibrillator is described that includes a dedicated optical image sensor that is configured as a barcode reader (BCR) module or optical character reader (OCR) module. The monitor defibrillator optical image sensor may be a camera or an image sensor such as a digital camera integrated circuit to capture images of barcodes or printed characters on items at the rescue scene. The monitor defibrillator preferably includes application software which automatically decodes images of barcodes or printed characters, and alerts the user when those images have been decoded and/or identified. The BCR module, the OCR module or the image sensor may reside within the main monitor defibrillator housing. Preferably, the optical image sensor resides within a second housing that is communicatively linked to the main housing with a data link via cable or wireless radio.

Accordingly to one object of the invention, a monitor defibrillator is described for recording parameters related to a medical treatment event in real time, comprising a patient monitoring circuit including a set of patient electrodes in communication with a controller operable to produce a patient electrocardiogram and to determine the need for a defibrillating shock, a patient therapy circuit controlled by the controller and operable to deliver the defibrillating shock, an optical sensor operable to obtain a barcode image, a memory, and a processor operable to decode the barcode image into barcode data and operable generate a patient record file into the memory comprising the barcode data and the time at which the barcode image was obtained. Preferably, the defibrillator monitor includes a display and an audio output to alert the user as to the success or lack of success of translating the barcode image into decoded data residing in memory.

Another object of the invention is a monitor defibrillator for recording parameters related to a medical treatment event in real time, comprising a patient monitoring circuit disposed within a first housing and including a connector for receiving a set of patient electrodes, and a controller in communication with the patient electrodes, the patient monitoring circuit operable to produce a patient electrocardiogram and to determine the need for a defibrillating shock, a patient therapy circuit disposed within the first housing and operable to deliver the defibrillating shock via the connector, an optical sensor disposed within a hand-portable second housing and operable to obtain a barcode image, a display disposed within the second housing, a wireless communications path disposed between the patient monitoring circuit in the first housing and the optical sensor in the second housing, a memory, and a processor operable to decode the barcode image into time-stamped barcode data and operable generate a patient record file into the memory comprising the barcode data and the patient electrocardiogram.

Yet another object of the invention is a method for recording data related to a medical treatment event in real time, comprising the steps of providing a defibrillator monitor having a processor, a memory, an optical image sensor such as a barcode reader, a user interface, an audible output, and a display. The method describes the steps of positioning an encoded graphic within the optical image sensor field of view, activating the optical image sensor by means of the user interface, imaging the encoded graphic with the optical image sensor, decoding the encoded graphic image into identifying data with the processor, and recording the identifying data into the memory as a record of the medical treatment event. The method concludes by issuing an audible indication at the audible output responsive to the completion of the decoding step and displaying a visual indication at the display responsive to the completion of the imaging step. The identifying data may be displayed as well. If the environment is too dark, a step of illuminating the encoded graphic may be included.

Another object of the invention is yet another method for recording data related to a medical treatment event in real time, comprising the steps of providing a defibrillator monitor having a processor, a memory, an optical image sensor such as a barcode reader that is separable from the defibrillator monitor, a user interface, an audible output, and a display. The method describes the steps of positioning the optical image sensor field of view to include an encoded graphic, activating the optical image sensor by means of the user interface, imaging the encoded graphic with the optical image sensor, decoding the encoded graphic image into identifying data with the processor, and recording the identifying data into the memory as a record of the medical treatment event. The method concludes by issuing an audible indication at the audible output responsive to the completion of the decoding step and displaying a visual indication at the display responsive to the completion of the imaging step. The identifying data may be displayed as well. If the environment is too dark, a step of illuminating the encoded graphic may be included.

In particular, two types of monitor/defibrillators that can benefit from automated data capture innovations as summarized above. In-hospital monitor defibrillators that are used by hospital personnel would be enabled to easily capture data related to in-hospital cardiac emergencies. Similarly, pre-hospital monitor defibrillators which are most often used by EMS personnel would be enabled to easily capture data related to out-of-hospital cardiac emergencies.

IN THE DRAWINGS

Figure 1:
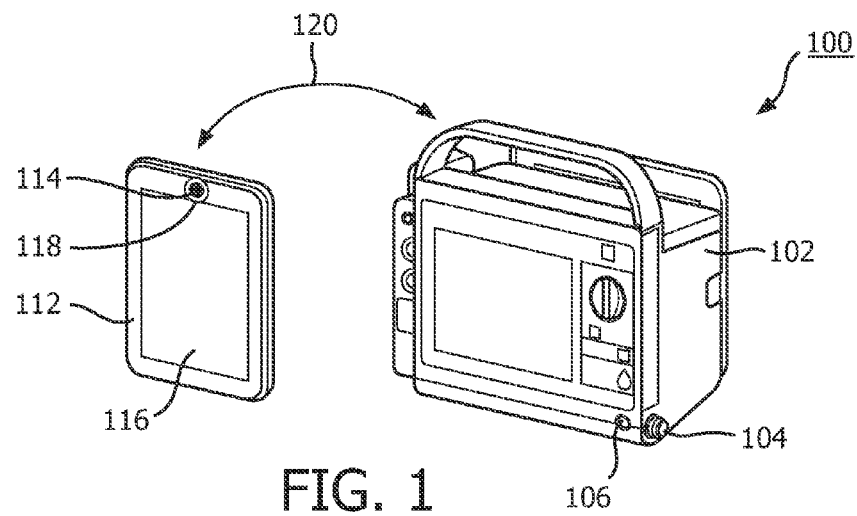
FIG. 1 is an illustration of a defibrillator for use with a patient suffering from a cardiac condition.

Now turning to the figures, FIG. 1 illustrates a defibrillator monitor 100 which is intended for use with a patient suffering from a cardiac condition. This embodiment of defibrillator 100 includes two main parts. Components within a first housing 102 include a connector 104 for electrically connecting external patient electrodes to internal patient monitoring and therapy circuitry. First housing 102 may include a display and an audio output 106 that provides the user with guidance and event status.

A second housing 112 on defibrillator monitor 100 is intended for use by the rescuer during the emergency and so is lightweight and portable. Second housing 112 is separately attached to first housing 102 in a stowage location on the back of housing 102. Second housing 112 includes an optical image sensor 114. An optional display 116 may be included on the housing to display the images and data captured by sensor 114. An optional light source 118 may be included and disposed adjacent to sensor 114 to provide illumination of target images in low light settings.

As can be seen in FIG. 1, the second housing 112 is arranged as a tablet-like device. The arrangement enables simple activation and use of the optical image sensor 114. As such, the second housing 112 can also contain other elements which can assist the user, such as video capture capability, a global positioning sensor (GPS), and/or wireless internet (Wi-Fi) connectivity.

The barcode reader or image sensor contained within the monitor/defibrillator housing can be of a number of different configurations. Several companies, such as Welch Allyn, Motorola, and others, manufacture dedicated optical image scanner modules that image and decode barcodes or printed characters. Dedicated scanners are small, embedded subsystems including a camera, illumination, microcontroller and firmware to acquire and decode images from barcodes or printed characters. An alternative to a dedicated BCR or OCR scanner module is a camera or discrete image sensor, such as a CMOS integrated circuit (IC) with lens for imaging, a discrete LED for illumination and software running on the monitor defibrillator processor to acquire and decode images from the barcodes or printed characters.

Figure 2:
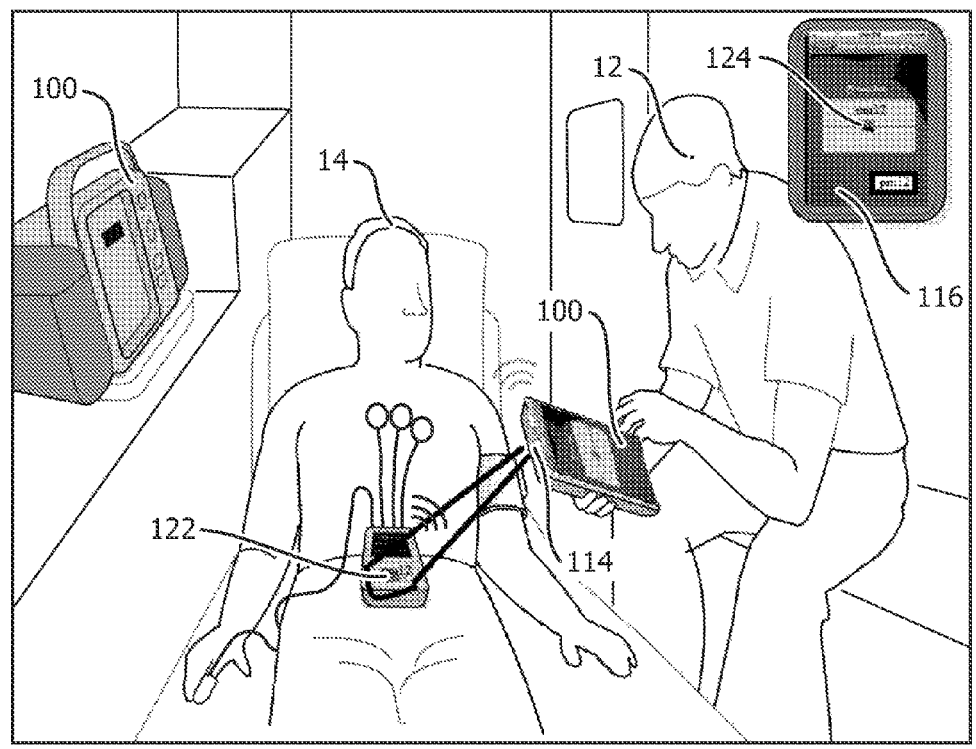
FIG. 2 illustrates the employment of a defibrillator according to one embodiment of the present invention.

Now turning to FIG. 2, shown is the employment of a defibrillator according to one embodiment of the present invention. A rescuer 12, here shown as a paramedic, deploys the monitor defibrillator 100 for use with a patient 14 in an out-of-hospital setting. The configuration of monitor defibrillator 100 shown here is similar to that described in FIG. 1. The rescuer 12 has separated the second housing of defibrillator monitor 100 from the main housing, and is using the optical image sensor 114 to capture identifying data contained within an encoded barcode, here a two-dimensional barcode 122 which identifies a particular patient monitoring module. The inset of FIG. 2 contains a clearer view of the display 116 that the rescuer is viewing on the second housing. The display 116 is currently displaying the barcode image 124 corresponding to barcode 122, so that the rescuer 12 has visual confirmation of the proper image capture and the proper decoding of the barcode.

In similar fashion, the rescuer 12 may position the image sensor 114 to capture the barcode on a patient identification card, an insurance card, a drug vial, a consumable medical product such as patient electrodes, or any similar item having identifying information. If image sensor 114 resides on the main housing, the barcode should of course be positioned within the sensor 114 field of view instead of repositioning the sensor 114 itself.

In operation, the rescuer 12 activates the reader module or image sensor via the user interface disposed on the second housing, such as via a touch screen on display 116. The scanner module or camera sensor in response images the item. A processor then decodes the barcode or printed character image into data. Then the monitor defibrillator 100 indicates the successful or unsuccessful data acquisition via an audio output or display 116 and optionally displays the result. The paramedic, after visually confirming the successful or unsuccessful data capture on the system display, can take further action. Once successful data capture is confirmed, the monitor defibrillator 100 appends the data into a medical event record that is held in system memory.

Another embodiment of the invention includes a scanner module or camera subsystem that is external to the main housing, and which may be enabled to acquire still images or video of the patient and or the event. The images may also be retained in the medical event record, or could be immediately transmitted to a hospital.

Figure 3:
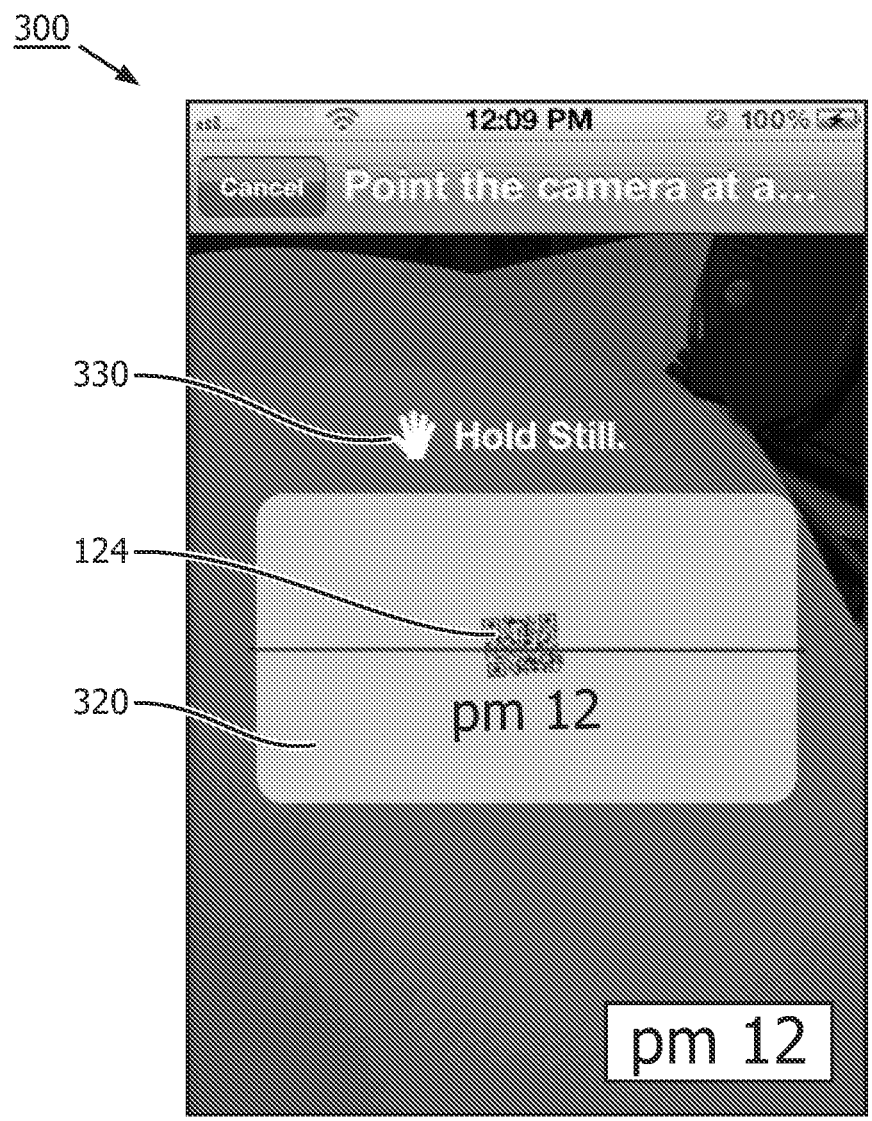
FIG. 3 illustrates one embodiment of a scan barcode screen.

FIG. 3 illustrates a more detailed view of a scan barcode screen 300 for assisting a user in obtaining information pertaining to equipment that is used in the medical treatment event. The optical image sensor and processor preferably is configured to capture and decode a one or two dimensional barcode-type identifier. These codes are intended to be applied to the exterior of the medical device in order to allow efficient tracking within the medical organization and for regulatory purposes. Barcode screen 300 exploits this situation by enabling the automatic detection and identification of such medical devices during the event. Once captured, the inventive system annotates the corresponding medical event log entry. The information provides follow-on opportunities to merge equipment-related event logs with the event logs generated by the defibrillator monitor 100. The equipment identifier is commonly the medical device serial number.

FIG. 3 shows a two-dimensional barcode disposed on the exterior of a wearable patient monitor that is in use at the medical treatment event shown in FIG. 2. Identifying data other than barcode data also falls within the scope of the invention. Although not shown, written text could also be imaged by the sensor 114 for decoding within the defibrillator monitor 100.

The user navigates to barcode screen 300 and activates sensor 114. A processor in defibrillator monitor 100 then automatically identifies the barcode image 124 in the target area 320. When the processor recognizes a readable barcode, it obtains the barcode via the sensor 114, decodes the barcode, and automatically records the device identifying information into the event record memory. The processor may simultaneously record the barcode read time into the event log.

If the two-dimensional barcode image 124 is too unstable to be accurately read, monitor defibrillator 100 issues a hold still prompt 330 for the user to steady the camera. After the image is successfully recognized and decoded, the monitor defibrillator 100 issues a confirmation prompt via display 116 or at the audio output 106, and may also display a subset of the decoded information such that the user is assured that the acquisition and decoding were correct.

Figure 4:
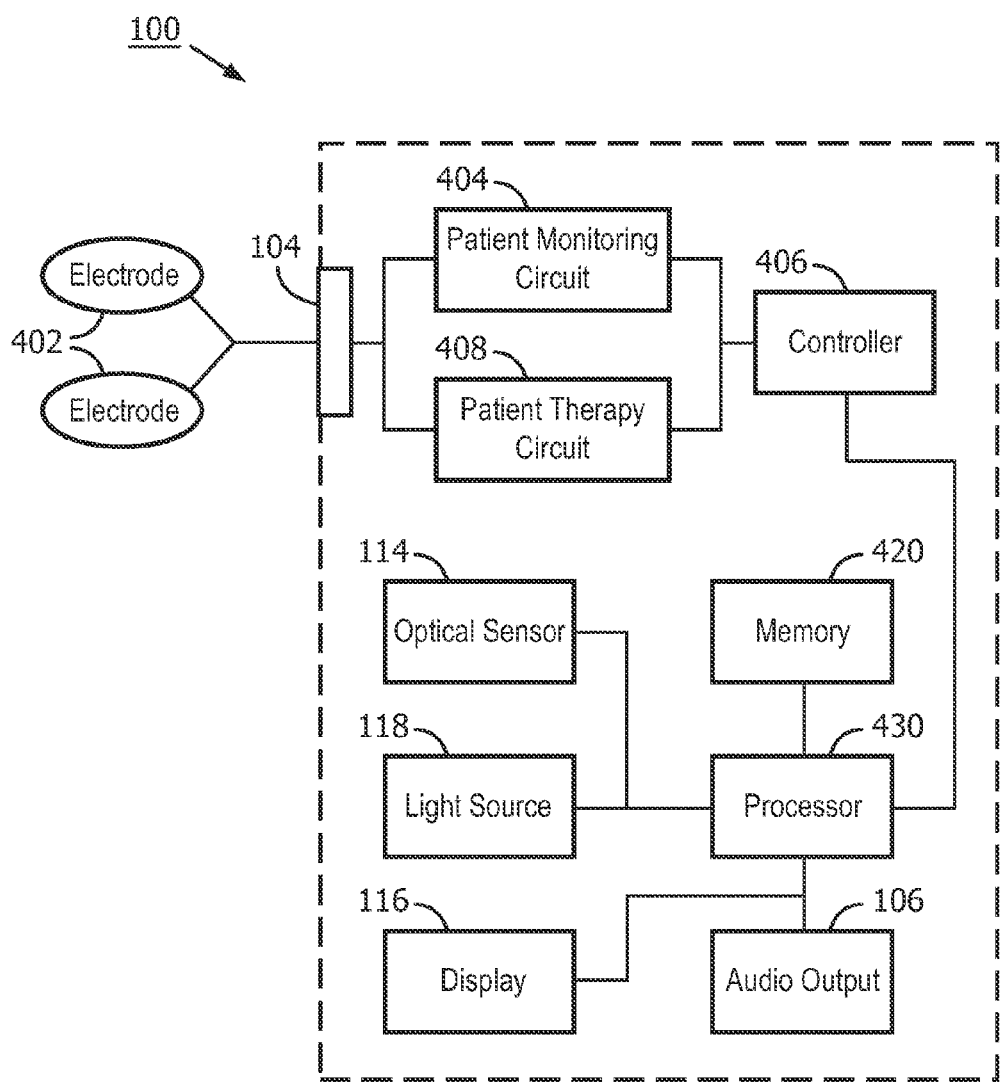
FIG. 4 is a view of a functional block diagram of a defibrillator monitor including an integrated optical image sensor for recording data during a medical treatment event.

FIG. 4 illustrates a view of a functional block diagram of a defibrillator monitor 100 according to one embodiment of the invention, including an integrated optical image sensor 114 for recording data during a medical treatment event. The FIG. 4 device is contained essentially in a single housing. Defibrillator monitor 100 includes a connector 104 which electrically connects a set of patient electrodes 402 to the device. Electrodes 402 may be monitoring electrodes, but are preferably multi-function electrodes that can monitor and provide electrotherapy to a patient. In the preferred electrode embodiment, a patient monitoring circuit 404 obtains an electrocardiographic (ECG) signal from the patient electrodes and provides a resulting ECG data record to a controller 406. Controller 406 in turn analyzes the ECG. If the ECG indicates that the cardiac rhythm is treatable by electrotherapy, controller 406 provides an audible and/or visual indication to the user, and prepares the device for delivering a shock via patient therapy circuit 408. Controller 406 also provides a record of the ECG, the shock decisions, and the subsequent treatment to a memory 420 for later analysis by administrators and follow-on treatment providers. In the FIG. 4 embodiment, the record is transferred to memory 420 via processor 430.

Processor 430 is operable to perform several functions. First, processor 430 decodes image data that is obtained by optical image sensor 114. Processor 430 also is the user interface control for a light source 118, which can be switched on by the user or automatically under low light conditions. Processor 430 may control display 116 and audio output 106 to provide guidance and status information relating to the encoded image data to the user, such as at the completion of decoding and display of the acquired data or subset of acquired data. Processor 430 also serves to integrate the ECG data received from controller 406 with data obtained from optical image sensor 114. For example, if the event data recorded in memory 420 is arranged chronologically, then processor 430 writes both of the ECG data and the image data into memory 420 based on the time that the data is obtained.

Figure 5:
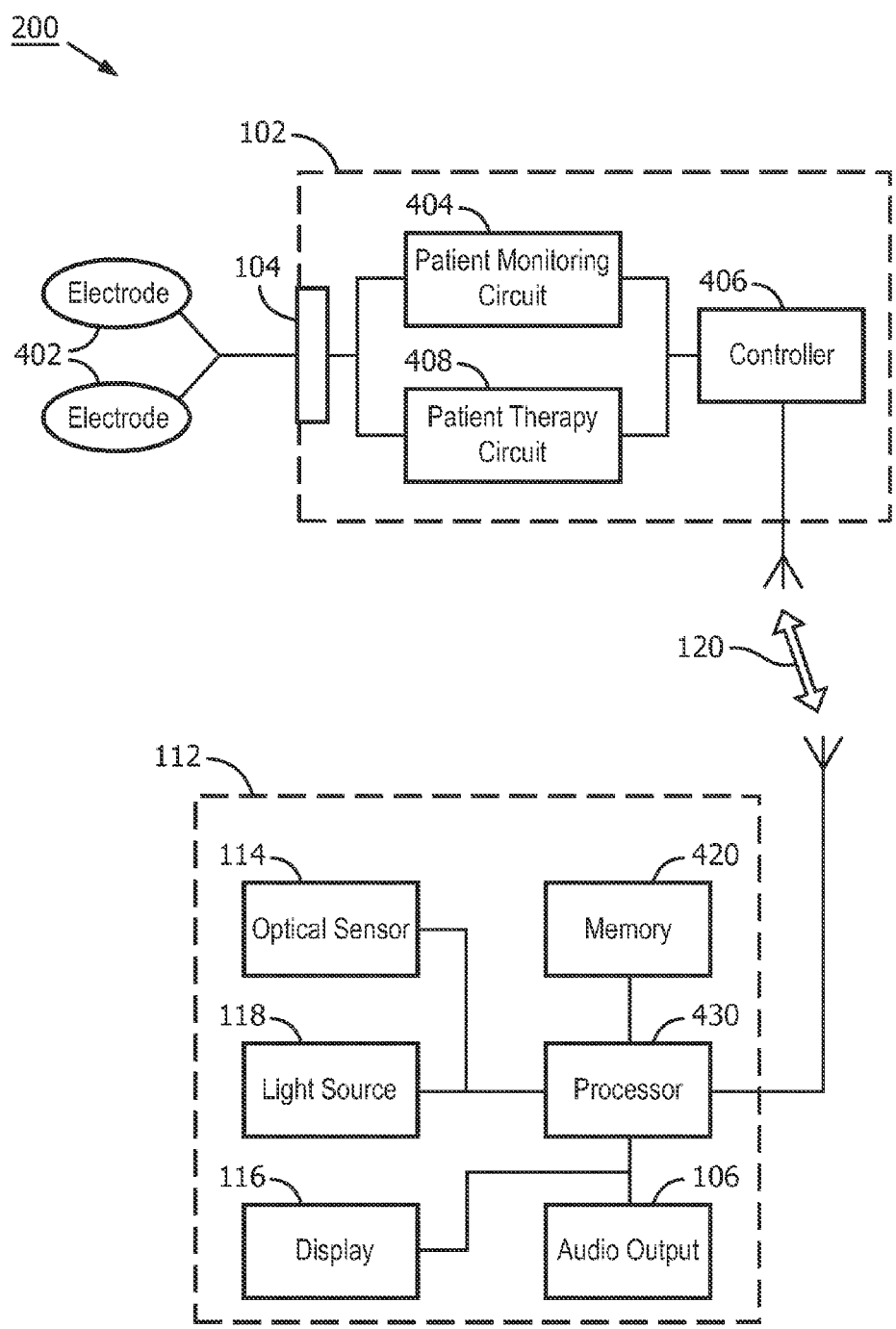
FIG. 5 is a view of a functional block diagram of a defibrillator monitor including a separable integrated optical image sensor for recording data during a medical treatment event.

FIG. 5 illustrates another functional block diagram of a defibrillator monitor 200 according to another embodiment of the invention. The FIG. 5 embodiment includes a separable integrated optical image sensor 114 for recording data during a medical treatment event. Each of the like-numbered components from FIG. 4 functions similarly to those in FIG. 5.

Because the defibrillator monitor 200 is in two parts, the FIG. 5 embodiment includes a communications means 120 between the patient monitoring circuitry of blocks 404, 406, 408 and the remaining components housed in a second housing 112. Communications means 120 is preferably a bidirectional wireless communications path, such as Wi-Fi, Bluetooth™, or a b-field communications path. Less preferred is a communications means 120 which is a wired communications cable between the circuits in the first housing 102 and second housing 112.

Also within the scope of the invention is the disposition of the processor 430, memory 420 and controller 406 relative to the housings and communications means 120. For example, memory 420 could be under control of controller 406 and residing in first housing 102.

Figure 6:
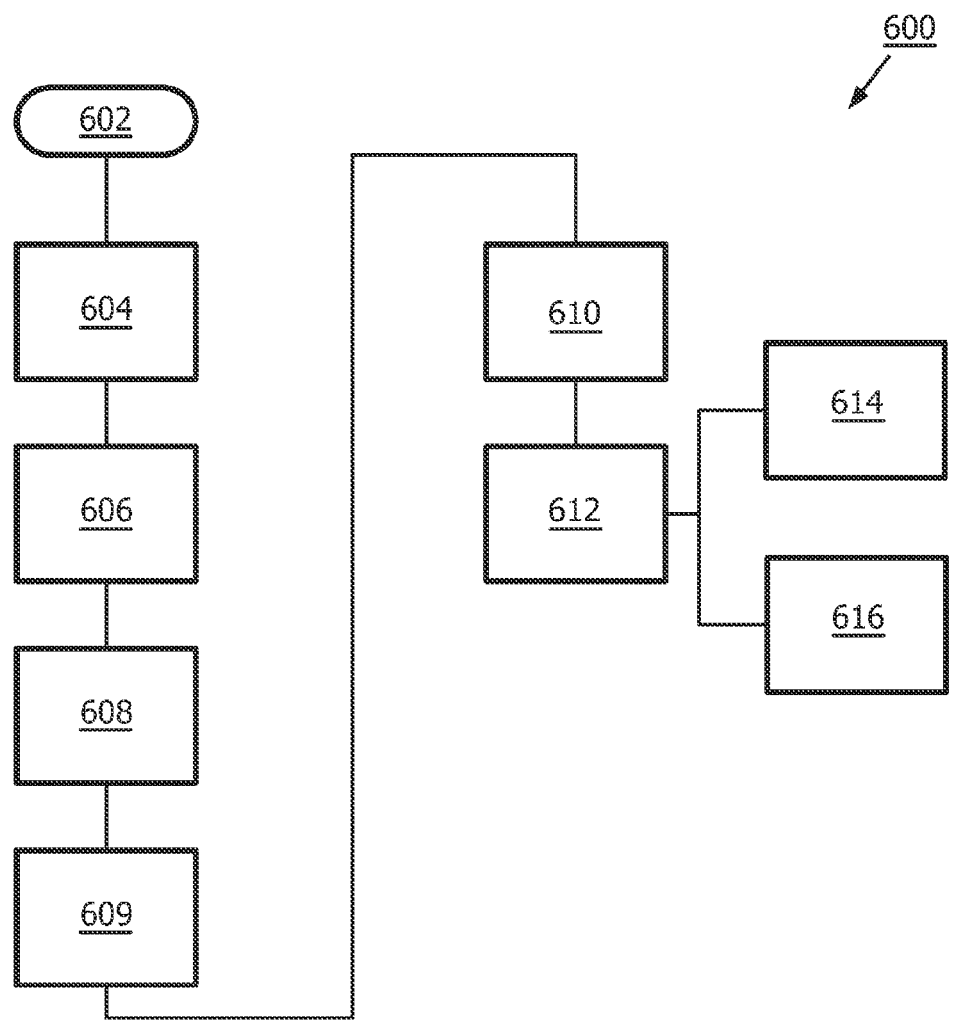
FIG. 6 illustrates one embodiment of a method for recording data related to a medical treatment event in real time.

FIG. 6 illustrates one embodiment of a method for recording data 600 related to a medical treatment event in real time. The method begins at step 602 wherein a defibrillator monitor is provided which includes a processor, a memory, an optical image sensor, a user interface, an audible output, and a display. A user positions an encoded graphic of interest within the optical image sensor field of view at step 604 and activates the optical image sensor at step 606 by means of the user interface. The activation step 604 could be accomplished by pressing a button or by touching an icon on a touch screen display. Activation step 604 could also be accomplished automatically under a software program control that recognizes barcode and optical character information as it enters the sensor field of view.

When the encoded graphic is positioned within the image sensor field of view, the encoded graphic is imaged at step 609. The imaging step can be either automatic or by a manual control. If the barcode or optical characters reside in a low-light environment, a prior illuminating step 608 may be necessary, wherein a light source that is placed adjacent to the image sensor is activated, again either manually or automatically, to provide sufficient illumination of the graphic.

After the barcode or optical character is imaged at step 609, it may be decoded at decoding step 610. Processor 430 or its equivalent automatically completes step 610. Preferably, feedback of the decoding step 610 completion is provided to the user via audible or visual indication. Of course, indication of a successful decoding may differ from an indication of a failed decoding step, which allows the user to proceed accordingly. The result of a successful decoding step 610 is a data record which identifies the imaged material.

The identifying data record is recorded into memory at step 612, preferably along with a time stamp of the imaging event. The identifying data record may be any of a patient identification, treatment protocol step, re-usable equipment employed during the event, drugs administered to the patient, and the like. The identifying data record could also be an inventory record of material staged with the defibrillator monitor for later use.

Issuing step 614 comprises issuing an audible indication at the defibrillator monitor that the decoding step has been completed. Issuing step 614 can also be enabled when the image is in view of the sensor, when imaging is complete, and when a record has been placed into memory. Step 614 may also be accompanied by an audible indication of the decoded identification itself.

Similarly, displaying step 616 comprises displaying a visual indication at the defibrillator monitor that the decoding step has been completed. FIG. 3 as previously described shows one embodiment of such a display. Displaying step 616 can also be enabled when the image is in view of the sensor, when imaging is complete, and when a record has been placed into memory. Step 616 may also be accompanied by the decoded identifier itself.

It is understood that the scope of the invention includes providing the issuing step 614 or the displaying step 616 prior to the recording step 612. For example, an audible prompt may be provided to the user immediately after the decoding step 610, accompanied by a display of the decoded image. Then, after the user determines that the decoded image is correct, she directs the device to conduct the recording step 612 by means of the user interface controls.

Figure 7:
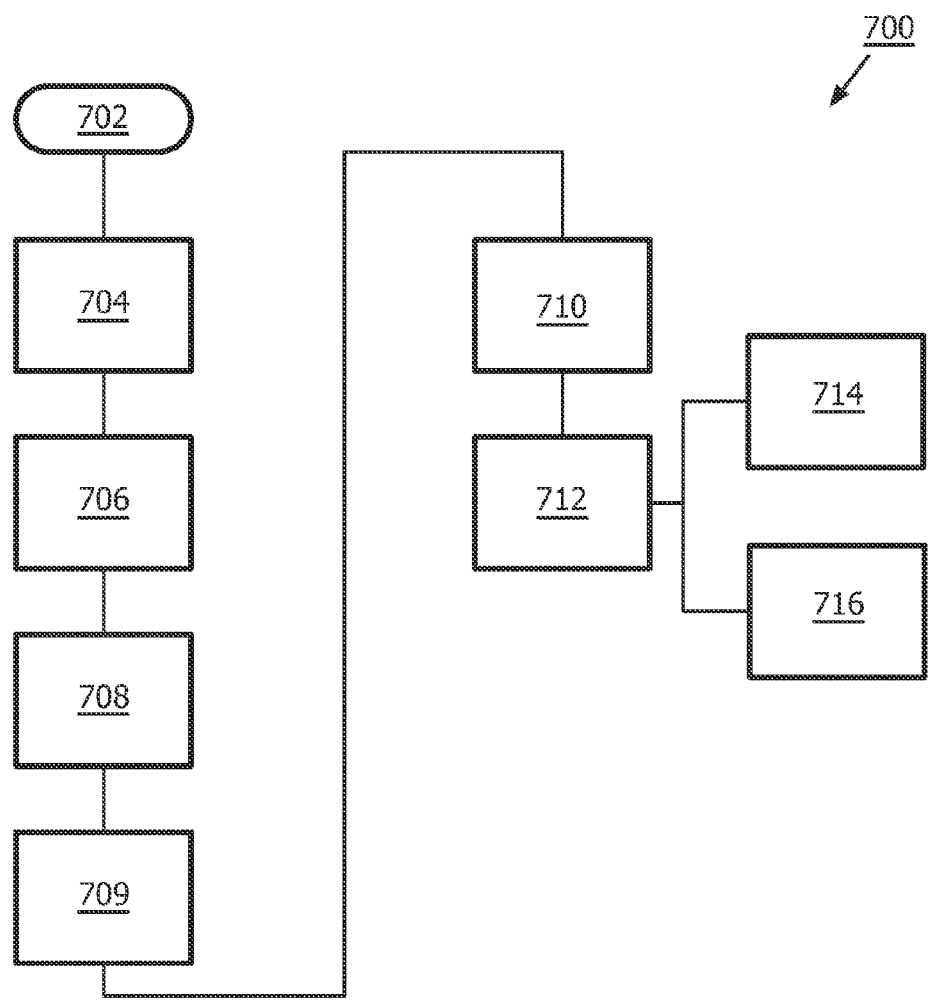
FIG. 7 illustrates another method for recording data related to a medical treatment event in real time.

FIG. 7 illustrates another method for recording data 700 related to a medical treatment event in real time. The method begins at step 702 wherein a defibrillator monitor is provided which includes a processor, a memory, an optical image sensor, a user interface, an audible output, and a display. Step 702 differs from the previous providing step 602 in that at least the optical image sensor is separate and separable from the defibrillator monitor. This physical configuration is previously described in relation to FIG. 5. In a preferred embodiment, the providing step provides that the optical image sensor, user interface and display are disposed in a circuit within a unitary housing that is separable from the defibrillator monitor, and wherein the providing step further comprises providing a wireless communications path between the circuit and the defibrillator monitor. Optionally, the processor and memory are also disposed in the unitary housing.

The image sensor being separate from the base unit defibrillator monitor, in the FIG. 7 embodiment, the user positions the optical image sensor field of view to include the encoded graphic of interest at step 704 and activates the optical image sensor at step 706 by means of the user interface. The activation step 704 could be accomplished by pressing a button or by touching an icon on a touch screen display. Activation step 704 could also be accomplished automatically under a software program control that recognizes barcode and optical character information as it enters the sensor field of view.

When the encoded graphic is properly positioned relative to the image sensor field of view, the encoded graphic is imaged at step 709. The imaging step can be either automatic or by a manual control. If the barcode or optical characters reside in a low-light environment, a prior illuminating step 708 may be necessary, wherein a light source that is placed adjacent to the image sensor is activated, again either manually or automatically, to provide sufficient illumination of the graphic.

After the barcode or optical character is imaged at step 709, it may be decoded at decoding step 710. Processor 430 or its equivalent automatically completes step 710. Preferably, feedback of the decoding step 710 completion is provided to the user via audible or visual indication. Of course, indication of a successful decoding may differ from an indication of a failed decoding step, which allows the user to proceed accordingly. The result of a successful decoding step 710 is a data record which identifies the imaged material.

The identifying data record is recorded into memory at step 712, preferably along with a time stamp of the imaging event. The identifying data record may be any of a patient identification, treatment protocol step, re-usable equipment employed during the event, drugs administered to the patient, and the like. The identifying data record could also be an inventory record of material staged with the defibrillator monitor for later use. Data received from the defibrillator monitor, such as ECG data, received via the wireless communications path may also be into the memory at step 712 along with the barcode data.

Issuing step 714 comprises issuing an audible indication at the defibrillator monitor that the decoding step has been completed. Issuing step 714 can also be enabled when the image is in view of the sensor, when imaging is complete, and when a record has been placed into memory. Step 714 may also be accompanied by an audible indication of the decoded identification itself.

Similarly, displaying step 716 comprises displaying a visual indication at the defibrillator monitor that the decoding step has been completed. FIG. 3 as previously described shows one embodiment of such a display. Displaying step 716 can also be enabled when the image is in view of the sensor, when imaging is complete, and when a record has been placed into memory. Displaying step 716 may also be accompanied by the decoded identifier itself.

It is understood that the scope of the invention includes providing the issuing step 714 or the displaying step 716 prior to the recording step 712. For example, an audible prompt may be provided to the user immediately after the decoding step 710, accompanied by a display of the decoded image. Then, after the user determines that the decoded image is correct, she directs the device to conduct the recording step 712 by means of the user interface controls.

Figure 8:
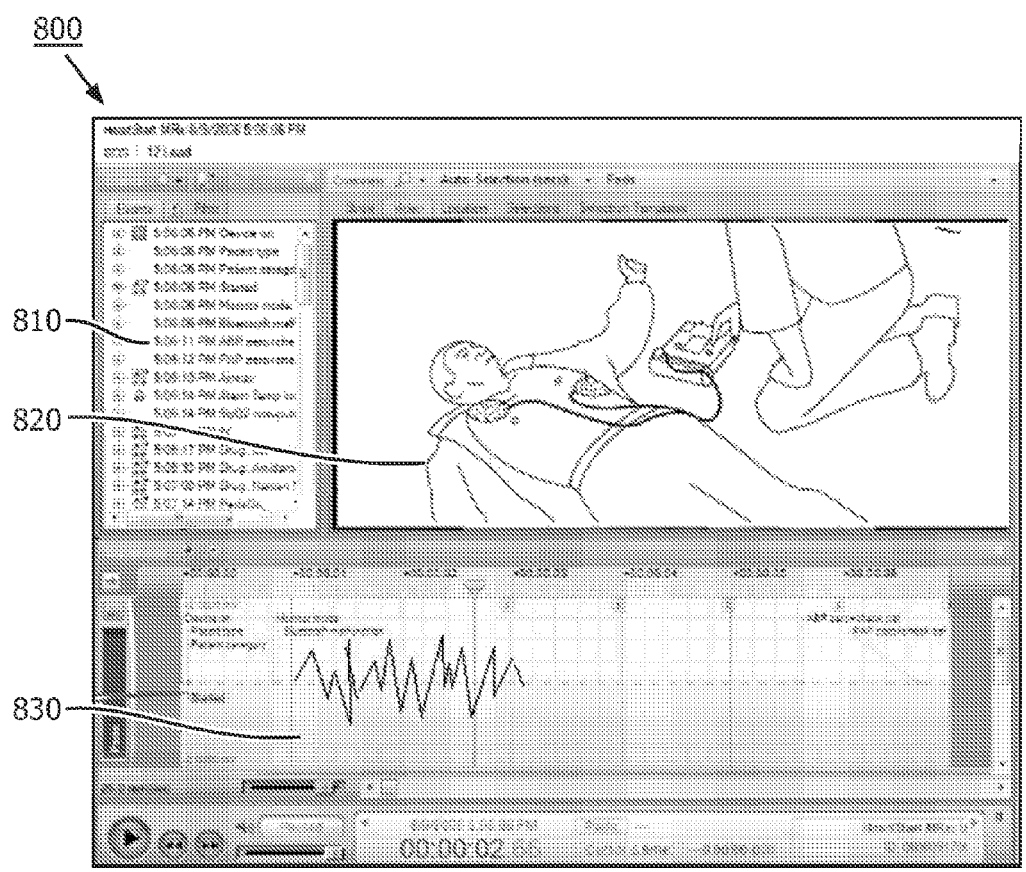
FIG. 8 illustrates an embodiment of a medical event review software application display including both cardiac data captured from a defibrillator monitor patient monitoring circuit and data obtained from an associated optical image sensor.

FIG. 8 illustrates an embodiment of a medical event review software application display including both cardiac data captured from a defibrillator monitor patient monitoring circuit and data obtained from an associated optical image sensor. A review and analysis program residing on a central computer arranges the event log data for post-event review by an administrator or manager. One such program that provides this functionality is the aforementioned Event Review software. FIG. 8 illustrates one embodiment of an annotation and video preview screen 800 that is a novel modification of an Event Review screen. In this embodiment, data and annotations from a defibrillator with its associated barcode and optical character data have been merged into an integrated event log for the medical treatment event prior to display. The merged annotations comprising decoded image data from the sensor and patient data from the patient monitor circuit are listed in chronological order in an event tree 810. The event tree may be scrolled, expanded to show more detailed information about the annotation, or collapsed as desired.

Some or all of the annotations appearing in the event tree 810 may also be plotted on a merged annotation timeline 830. The timeline 830 is a more graphical-appearing event record generally having a sweep bar that marks the current time. In the FIG. 8 embodiment, an ECG obtained from the defibrillator data and the barcode data may be superimposed on the timeline 830. Audio from the event may also be played as the time bar progresses.

One additional feature of the annotation and video preview screen 800 is the simultaneous display of recorded medical event video 820 that is synchronized with the progress of the annotation timeline 830. An optional video record as obtained from the defibrillator monitor image sensor may be included in the medical event record. Standard video controls may be provided for the user to manipulate the playback.

Modifications to the device, software, and displays as described above are encompassed within the scope of the invention. For example, the appearance and arrangement of displays and the particular location of each of the circuits may differ somewhat than shown in the particular embodiments. Different user controls which are incorporated into the second housing 112, but which perform essentially the same functions as described also fall within the scope of the invention.

Table of the Elements

| Element Number | Element Name |
|---|---|
| 12 | rescuer |
| 14 | patient |
| 402 | electrodes |
| 100 | defibrillator monitor |
| 116 | display |
| 114 | optical image sensor |
| 102 | first housing |
| 104 | connector |
| 106 | audio output |
| 430 | processor |
| 420 | memory |
| 112 | second housing |
| 114 | optical image sensor |
| 116 | display |
| 118 | light source |
| 119 | audio record |
| 120 | communications means |

-continued

Table of the Elements

| Element Number | Element Name |
|---|---|
| 300 | scan barcode screen |
| 122 | barcode |
| 124 | barcode image |
| 320 | target area |
| 330 | hold still prompt |
| 406 | controller |
| 404 | patient monitoring circuit |
| 408 | patient therapy circuit |
| 600 | method for recording data |
| 602 | providing defibrillator monitor step |
| 604 | positioning an encoded graphic step |
| 606 | activating image sensor step |
| 609 | imaging the encoded graphic step |
| 608 | illuminating step |
| 610 | decoding the graphic step |
| 612 | recording data step |
| 614 | issuing audible indication step |
| 616 | displaying visual indication step |
| 700 | method for recording data |
| 702 | providing defibrillator monitor step |
| 704 | positioning a field of view step |
| 706 | activating image sensor step |
| 709 | imaging the encoded graphic step |
| 708 | illuminating step |
| 710 | decoding the graphic step |
| 712 | recording data step |
| 714 | issuing audible indication step |
| 716 | displaying visual indication step |
| 800 | medical treatment event record |
| 810 | event log listing |
| 820 | optical imager record |
| 825 | patient monitoring record |

What is claimed is:

1. A monitor defibrillator for recording parameters related to a medical treatment event in real time, comprising:
   a patient monitoring circuit within a first housing including a set of patient electrodes in communication with a controller operable to produce a patient electrocardiogram and to determine the need for a defibrillating shock;
   a patient therapy circuit within the first housing controlled by the controller and operable to deliver the defibrillating shock;
   an optical sensor within a second housing, the second housing being separably attached to the first housing, the optical sensor being operable to obtain a barcode image, wherein the optical sensor comprises a dedicated optical image scanner module that includes an embedded subsystem of a camera, illumination, microcontroller and firmware to acquire and decode images from barcodes or printed characters;
   a memory disposed within the second housing;
   a processor within the second housing operable to decode the barcode image into barcode and printed character data; and
   a wireless communicating means configured to communicate bi-directionally between (i) the controller in the first housing and (ii) the processor in the second housing,
   wherein controller in the first housing is operable to transmit, via the wireless communicating means, (i) patient electrocardiogram data and (ii) a record of the defibrillating shock, to the processor in the second housing, and
   wherein the processor in the second housing is operable to (i) receive (i)(a) the patient electrocardiogram data and the record of the defibrillating shock and (i)(b) a time stamp from an internal clock reference of the patient monitoring circuit based on a time at which the barcode image was obtained, (ii) issue, via a display or an audio output within the second housing, (ii)(a) a first indication that the bar code was acquired and decoded correctly or (ii)(b) a second indication, different from the first indication, of a failed decoding step, and (iii) record, in response to a confirmation of successful data capture via the first indication, (iii)(a) the decoded barcode and printed character data and (iii)(b) the patient electrocardiogram data, the record of the defibrillating shock, and the time stamp, into a patient record file stored in the memory.

2. The monitor defibrillator of claim 1, wherein the wireless communicating means is one of a bidirectional wireless Wi-Fi, wireless Bluetooth, and wireless b-field communications path.

3. The monitor defibrillator of claim 1, further comprising a light source disposed adjacent to the optical sensor and operable to illuminate the barcode image.

4. The monitor defibrillator of claim 1, wherein the optical sensor is further operable to obtain an image of a written character, and further wherein the processor is operable to decode the image of the written character into identifying data and to record the identifying data into the patient record file.

5. The monitor defibrillator of claim 4, wherein the image of the written character is obtained from one of a driver's license, an insurance card, a defibrillator monitor disposable electrode, or a pharmaceutical product.

6. A monitor defibrillator for recording parameters related to a medical treatment event in real time, comprising:
   a patient monitoring circuit disposed within a first housing and including
      a connector for receiving a set of patient electrodes, and
      a controller in communication with the patient electrodes,
      the patient monitoring circuit operable to produce a patient electrocardiogram and to determine the need for a defibrillating shock;
   a patient therapy circuit disposed within the first housing and operable to deliver the defibrillating shock via the connector;
   an optical sensor disposed within a second housing, the second housing being separably attached to the first housing, the optical sensor being operable to obtain a barcode image, wherein the optical sensor comprises a dedicated optical image scanner module that includes an embedded subsystem of a camera, illumination, microcontroller and firmware to acquire and decode images from barcodes or printed characters;
   a display disposed within the second housing;
   a wireless communications path disposed between the patient monitoring circuit in the first housing and the optical sensor in the second housing;
   a memory disposed within the second housing; and
   a processor disposed within the second housing operable to decode the barcode image into time-stamped barcode and printed character data with a time stamp; and
   a wireless communications path for bi-directional communication between the controller in the first housing and the processor in the second housing,
   wherein the controller in the first housing is operable to transmit, via the wireless communications path, (i)

patient electrocardiogram data and (ii) a record of the defibrillating shock to the processor in the second housing, and wherein the processor in the second housing is operable to (i) receive (i)(a) the patient electrocardiogram data and the record of the defibrillating shock and (i)(b) the time stamp, obtained from an internal clock reference of the patient monitoring circuit based on a time at which the barcode image was obtained, and operable to (ii) issue, via the display or an audio output within the second housing, (iii)(a) a first indication that the bar code was acquired and decoded correctly or (iii)(b) a second indication, different from the first indication, of a failed decoding step and (iii) record, in response to a confirmation of successful data capture via the first indication, (iii)(a) the time-stamped decoded barcode data and printed character data and (iii)(b) the patient electrocardiogram data, the record of the defibrillating shock, and the time stamp, into a patient record file stored in the memory.

* * * * *